United States Patent [19]

Harker

[11] Patent Number: 5,085,759
[45] Date of Patent: Feb. 4, 1992

[54] APPARATUS FOR RAPID BIOLOGICAL OXIDATION DEMAND OF LIQUIDS

[75] Inventor: Alan R. Harker, Stillwater, Okla.

[73] Assignee: Duncan Instrument Company, Oklahoma City, Okla.

[21] Appl. No.: 436,450

[22] Filed: Nov. 13, 1989

[51] Int. Cl.⁵ ............................................ G01N 27/40
[52] U.S. Cl. ................................ 204/408; 204/222; 204/225; 204/415
[58] Field of Search ............... 204/1 P, 1 T, 415, 222, 204/225, 408

[56] References Cited

U.S. PATENT DOCUMENTS

| | | | |
|---|---|---|---|
| 3,088,905 | 5/1963 | Glover | 204/415 |
| 3,427,238 | 2/1969 | Myers et al. | 204/405 |
| 3,505,195 | 4/1970 | Nielsen et al. | 204/415 |
| 3,518,179 | 6/1970 | Bleak et al. | 204/415 |
| 3,598,711 | 8/1971 | Flais | 204/427 |
| 4,182,666 | 1/1980 | Dickinson et al. | 204/415 |
| 4,518,477 | 5/1985 | Wright et al. | 204/409 |
| 4,842,709 | 6/1989 | Mayeaux | 204/430 |
| 4,911,794 | 3/1990 | Parce et al. | 204/415 |

*Primary Examiner*—T. Tung
*Attorney, Agent, or Firm*—Glen M. Burdick; Bill D. McCarthy

[57] ABSTRACT

An apparatus is provided for rapidly determining the biochemical oxidation demand (BOD) of a liquid at an on-site location. The apparatus includes a cell body member having a vertically extensive plunger chamber formed therein and a sample holding chamber communicating therewith, a dissolved oxygen sensor for generating a signal in proportion to the amount of dissolved oxygen content in a liquid sample and a culture medium disposed in the sample holding chamber, and a tubular plunger member extensive into the plunger chamber for supporting the dissolved oxygen sensor such that the dissolved oxygen sensor extends into the sample chamber and into contact with the liquid sample and the culture medium. A temperature control assembly, which includes a thermocouple, an internal heat sink element, and a Peltier cell device, is supported by the cell body member such that the internal heat sink element is in close proximity to the sample holding chamber and cooperates with the Peltier cell device for selectively heating and cooling the culture medium and liquid sample in order to maintain same at a predetermined temperature. A computer, programmed to monitor the temperature of the culture medium and the liquid sample via input signals from the thermocouple and provide control signals to the Peltier cell device to maintain the temperature of the culture medium and liquid sample at a substantially constant value, is also programmed to interpret signals from the dissolved oxygen sensor so that the biochemical oxidation demand (BOD) of the liquid sample can be determined.

20 Claims, 4 Drawing Sheets

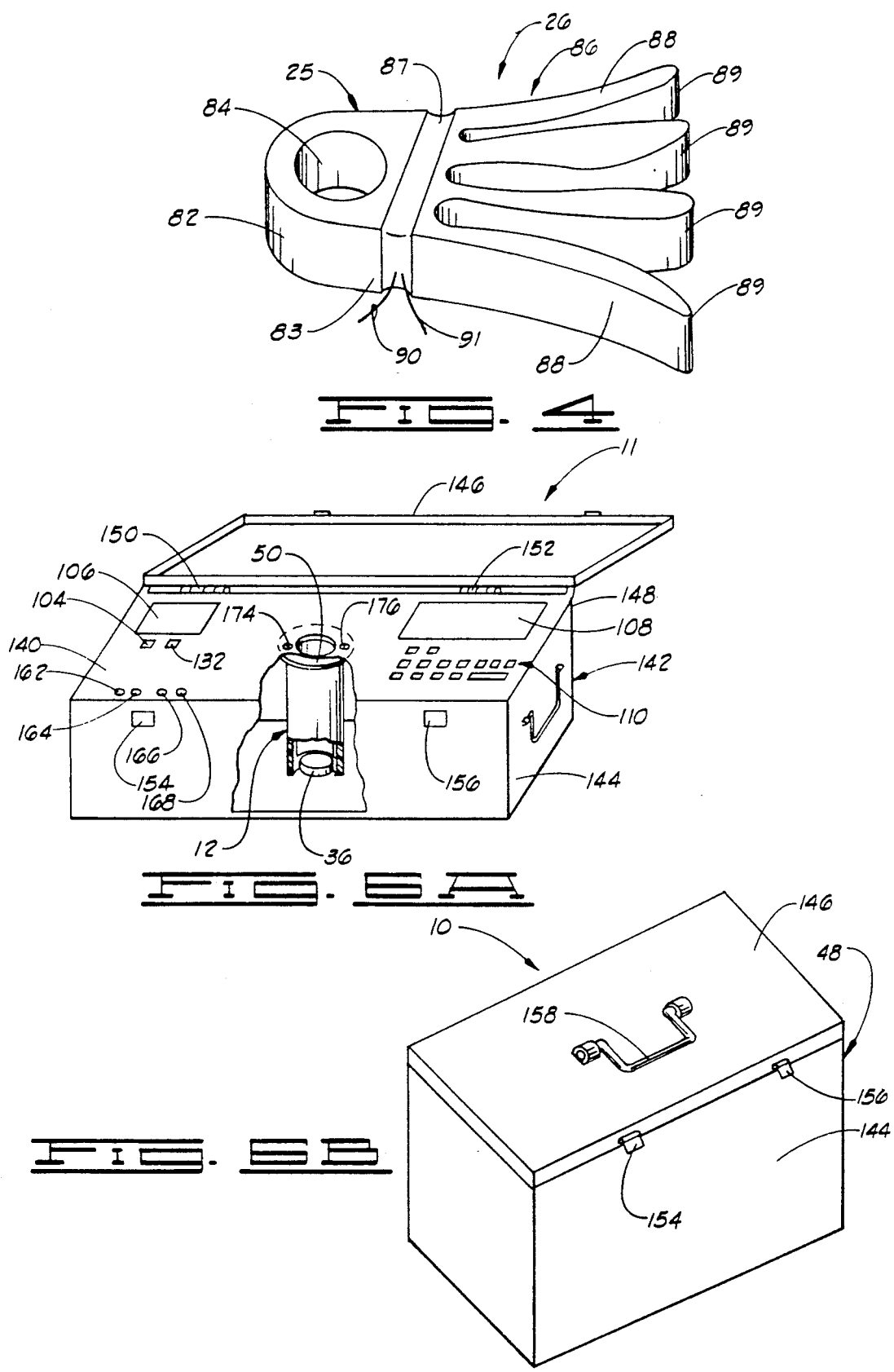

APPARATUS FOR RAPID BIOLOGICAL OXIDATION DEMAND OF LIQUIDS

BACKGROUND OF THE INVENTION

1. Field of the Invention

The present invention relates generally to the field of aquatic pollution, and more particularly, but not by way of limitation, to an apparatus for rapidly determining the biochemical oxygen demand of a liquid at an on-site location.

2. Brief Description of the Prior Art

Biochemical oxidation demand (BOD) is widely used in measuring aquatic pollution. For example, the performance of wastewater treatment plants is generally monitored by measuring the efficiency of BOD removal.

One of the major problems encountered in use of the conventional BOD test is that the test generally requires five or more days to run, a time period which is too long for use in process control. Other tests, such as the total organic carbon (TOC) and chemical oxidation demand (COD) measure total organic matter, but such tests do not provide a valid measure of biologically degradable organic matter.

A key feature of the BOD test as a measure of the total biologically degradable organic matter is sequential uptake, commencing with labile and ending with refractory compounds. Studies of biofilms have suggested that the oxidation of complex mixtures of organics in fully oxygenated biofilms proceeds sequentially as substrate diffuses into the biofilm in a manner similar to uptake in plug-flow activated sludge units or in the conventional BOD test. As the result of such studies, biofilm BOD electrodes have been developed for use in rapid measurements of wastewater samples.

While initial studies using the biofilm BOD electrode or probe have exhibited favorable results, the use of such probes to make rapid BOD measurements at on-site locations has been difficult because of the auxiliary equipment required in carrying out the test. Further, the biofilm BOD electrode or probe suffers from the disadvantage that it is not acclimated to the effluent being tested, and is unstable.

Thus, while some advance has been made in the art in developing apparatus for the rapid BOD measurements, the need still remains for an apparatus which can be employed to rapidly measure the BOD of a liquid sample at an on-site location, which is dependable and simple in operation, easily transported, and economical to manufacture. It is to such apparatus that the present invention is directed.

SUMMARY OF THE INVENTION

According to the present invention a portable apparatus for rapidly determining the biochemical oxygen demand (BOD) of a liquid at an on-site location is provided which includes a cell body member having a vertically extensive plunger chamber and a sample holding or test chamber communicating therewith, a dissolved oxygen sensor electrode supported within the cell body member so as to be in contact with a liquid sample and culture medium disposed within the sample holding chamber, and a temperature sensor and control assembly for providing signals indicative of the temperature of the liquid sample and the culture medium in the sample holding chamber and for selective heating and cooling same in order to maintain the liquid sample and culture medium at a predetermined temperature. The dissolved oxygen sensor electrode and temperature sensor and control assembly are operably connected to a microcomputer which is programmed to control the temperature of the liquid sample and the culture medium, monitor the output of the dissolved oxygen sensoring electrode, and thereafter compute the biochemical oxygen demand of the liquid sample.

An object of the present invention is to provide a portable apparatus for measuring the biochemical oxygen demand of a liquid sample.

Another object of the present invention, while achieving the before stated object, is to provide an improved self-contained apparatus for use in measuring the biochemical oxygen demand of wastewater to determine aquatic pollution.

Yet another object of the present invention, while achieving the before stated objects, is to provide an improved apparatus for rapid on-site measurements of the biochemical oxygen demand of a liquid which is durable, economical to manufacture, requires minimal user training, and which overcomes the deficiencies of the prior art devices Other objects, features and advantages of the present invention will become apparent from the following detailed description when read in conjunction with the drawings and appended claims.

BRIEF DESCRIPTION OF THE DRAWINGS

FIG. 4 is an enlarged, perspective view of a Peltier cell device connected to an internal heat sink element for selectively heating and cooling liquid sample and culture medium in the cell body member in order to maintain same at a predetermined temperature.

FIG. 6A is a partially cutaway, perspective view of a portable apparatus schematically shown in FIG. 5 for rapidly determining the biochemical oxygen demand of a liquid at a on-site location wherein a closure member of a housing of the apparatus is in an open position.

FIG. 6B is a perspective view of the housing of FIG. 6A wherein the closure member is in a closed, locked position.

DETAILED DESCRIPTION

Figure 1:
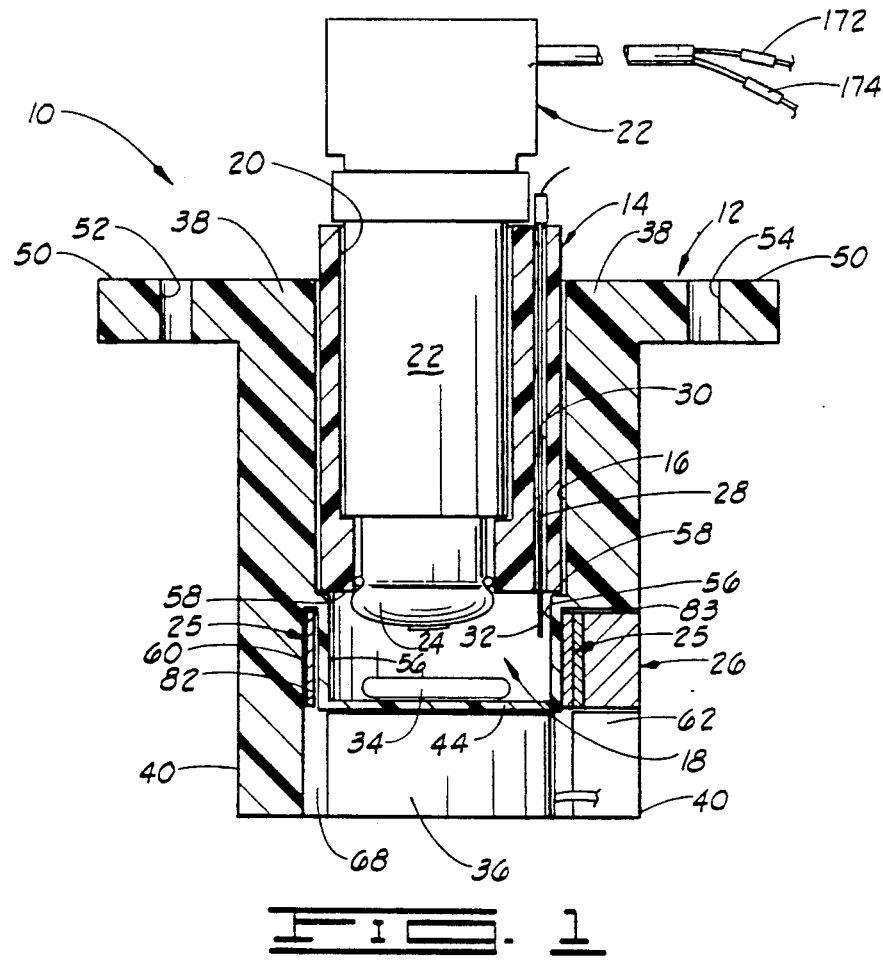
FIG. 1 is an enlarged, cross sectional view of a cell assembly for use in obtaining rapid measurements indicative of the biochemical oxygen demand of a liquid.

Referring now to the drawings, and more particularly to FIG. 1, a cell assembly 10 of an apparatus 11 (see FIGS. 5, 6A and 6B) of the present invention is illustrated The apparatus 11 permits one to rapidly determine the biochemical oxygen demand of a liquid at an on-site location is illustrated.

The cell assembly 10 comprises a cell body member 12, a tubular plunger member 14 insertable a selected distance into a plunger chamber 16 formed in the cell body member 12 so that a sample holding or test chamber 18 is formed in a lower portion of the plunger chamber 16 substantially as shown. The tubular plunger member 14 is provided with an electrode receiving bore 20 extensive therethrough adapted to supportingly receive a dissolved oxygen sensor or electrode 22 so that a distal end 24 of the electrode 22 is disposed within the sample holding chamber 18 and into contact with a culture medium and liquid sample disposed therein. The cell body member 12 and the tubular plunger member 14 are constructed such that in an assembled position the sample holding chamber 18 formed in the lower portion of the plunger chamber 16 is provided with a preselected volume of about 2 milliliters.

In order to monitor and control the temperature of the culture medium and liquid sample during measurements of the dissolved oxygen present in the culture medium and liquid sample by the electrode 22, the cell assembly 10 is provided with an internal heat sink element 25 connected to a thermoelectric device 26 (which operates by the Peltier effect), and a temperature sensor, such as a thermocouple 28. The internal heat sink element 25 is supported by the cell body member 12 in close proximity to the sample holding chamber 18 so that upon activation of the thermoelectric device 26, the culture medium and liquid sample in the sample holding chamber 18 can be selectively heated or cooled in order to maintain the culture medium and liquid sample at a substantially constant, predetermined temperature.

The thermocouple 28, which measures the temperature of the culture medium and liquid sample in the sample holding chamber 18, is disposed through a thermocouple receiving bore 30 extending longitudinally through the tubular plunger member 14 so as to be spatially disposed relatively to the electrode receiving bore 20. A distal end 32 of the thermocouple 28 (which extends into the sample holding chamber 18 and into contact with the culture medium and liquid sample) generates signals indicative of the temperature of the culture medium and liquid sample.

The culture medium and liquid sample in the sample holding chamber 18 are desirably stirred at a constant rate so that a substantially uniform, homogeneous mixture of such constituents is maintained during the testing procedure. To achieve the desired agitation of the culture medium and liquid sample, a micro stir bar 34 is positioned within the sample holding chamber 18 and a magnetic stir motor 36 is positioned below the sample holding chamber 18. Thus, upon activation of the magnetic stir motor 36 the micro stir bar 34 is caused to rotate and thereby stir the culture medium and liquid sample to provide the desired homogeneous mixture of same.

As will be more clearly set forth hereinafter, the dissolved oxygen sensor or electrode 22, the thermoelectric device 26, the thermocouple 28 and the magnetic stir motor 36 are operably connected to a microcomputer programmed to determine the biochemical oxygen demand of the liquid sample in the presence of the culture medium disposed within the sample holding chamber 18 from data received from the dissolved oxygen sensor 22 under the conditions prescribed for the thermoelectric device 26 by input signals provided by the thermocouple 28.

Figure 2A:
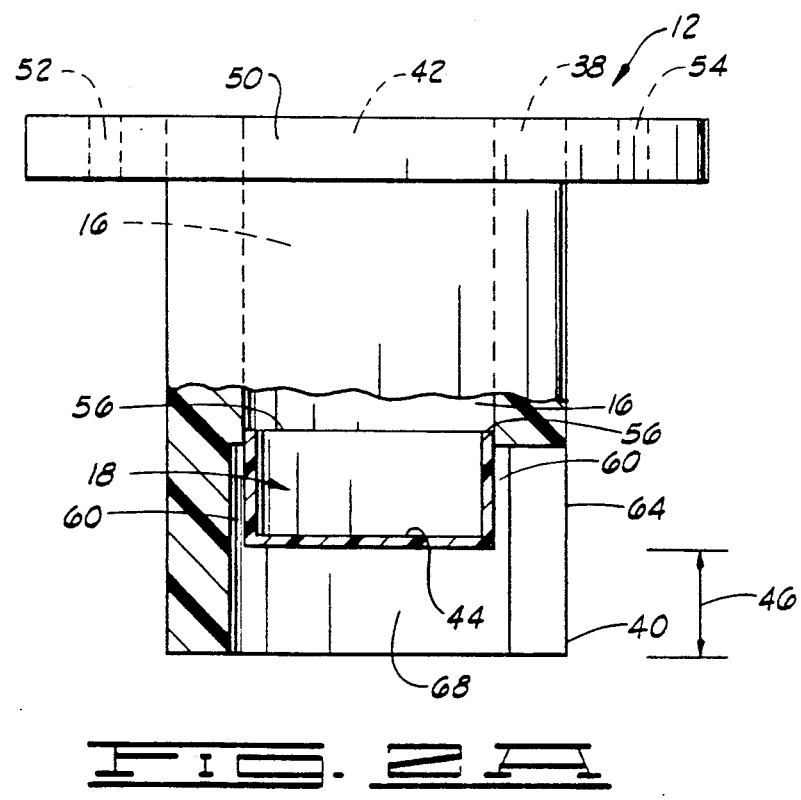
FIG. 2A is an enlarged, side elevational view, partially in cross section, of a cell body member of the cell assembly of FIG. 1.
Figure 2B:
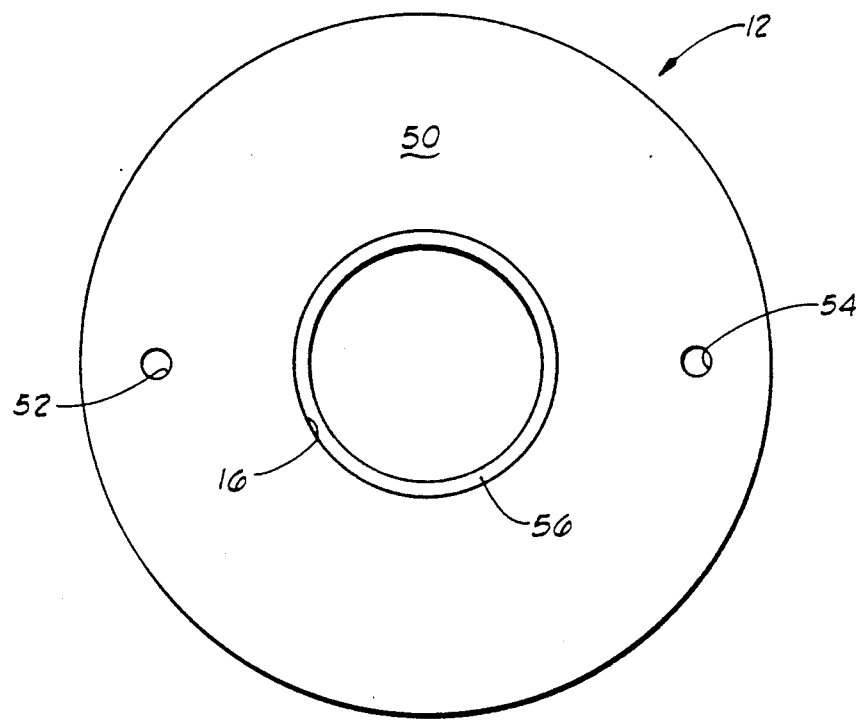
FIG. 2B is a top plan view of the cell body member of FIG. 2A.

Referring more specifically to FIGS. 2A and 2B, the cell body member 12 is characterized as having an upper end portion 38 and an opposed lower portion 40. The plunger chamber 16 (which is vertically disposed within the cell body member 12) is provided with an open upper end 42 and a closed lower end 44 such that the closed lower end 44 terminates a distance 46 from the lower end portion 40 of the cell body member 12 substantially as shown. To secure the cell body member 12 in a stable position in a housing 48 of the apparatus 11 (see FIG. 6A), the cell body member 12 is provided with peripherally extensive flange 50 disposed about its upper end portion 38. A plurality of spatially disposed vertically extensive openings 52, 54 are positioned within the flange 50 to assist in securing the cell body member 12 within the housing 48 as will be more fully discussed hereinafter.

The cell body member 12 is further provided with a peripherally extensive plunger stop shoulder 56 disposed near the closed lower end 44 of the plunger chamber 16 so as to abuttingly engage a lower end 58 of the tubular plunger member 14 when same is positioned within the plunger chamber 16 substantially as shown in FIG. 1. As will be more clearly set forth hereinafter, the plunger stop shoulder 56 and the lower end 58 of the tubular plunger member 14 cooperate with the closed lower end 44 of the plunger chamber 16 to define the sample holding or test chamber 18. Further, the unique structure of the cell body member 12 and the tubular plunger member 14 cooperate to insure that the volume of the sample holding chamber 18 is maintained at a predetermined, constant volume when the tubular plunger member 14, the dissolved oxygen sensor or electrode 22 and the cell body member 12 are in an assembled position.

To secure and support the internal heat sink element 25 in close proximity to the sample holding chamber 18 of the cell body member 12 so that the liquid sample and culture medium placed therein can be selectively heated and cooled by the thermoelectric device 26 in order to maintain the culture medium and liquid sample at a predetermined temperature (while measurements as to the amount of dissolved oxygen present in the culture medium and liquid sample are being made by the electrode 22), the cell body member 12 is provided with an annular space 60 disposed about the sample holding chamber 18 and an elongated slot 62 which extends from the lower end portion 40 of the cell body member 12 upwardly along one side wall 64 of the cell body member 12 so as to openly communicate with the annular space 60. The internal heat sink element 25 is positioned within the annular space 60 (which constitutes an internal heat sink for the sample holding chamber 18) so that the internal heat sink element 25 is disposed about the sample holding chamber 18 substantially as shown in FIG. 1.

The thermoelectric device 26 (which is connected to the internal heat sink element 25 by any suitable means such as an adhesive material) extends through the elongated slot 62 (which functions as an external heat sink for the sample holding chamber 18). As will be described in more detail hereinafter, the thermoelectric device 26 is connected to a microcomputer 66 (see FIG. 6) programmed to monitor and control the temperature of the culture medium and liquid sample in the sample holding chamber 18 at a predetermined temperature during measurements to determine the dissolved oxygen content of the culture medium and the liquid sample in the sample holding chamber 18.

The cell body member 12 is further provided with a centrally disposed recess 68 extending upwardly from the lower end portion 40 thereof so as to openly communicate with the annular space 60. The magnetic stir motor 36 is positioned within the recess 68 so that the magnetic stir motor 36 abuttingly engages the closed lower end 44 of the plunger chamber 16 and cooperates in supporting the cell body member 12 in a stable position. Further, upon activation of the magnetic stir motor 36 the micro stir bar 34 disposed within the sample holding chamber 18 is caused to rotate thereby insuring that the culture medium and the liquid sample are sufficiently agitated to provide a substantially homogeneous admixture during measurements thereon from which the biochemical oxygen demand of the homogeneous mixture can be computer by the microcomputer 66.

As previously stated, the tubular plunger member 14 and the dissolved oxygen sensor or electrode 22 cooperate with the cell body member 12 to provide the sample holding chamber 18 with a constant, predetermined volume. As shown in FIG. 3B, the tubular plunger member 14 (in addition to the electrode receiving bore 20 and the thermocouple receiving bore 30) is provided with a spatially disposed fluid injection bore 70 so that a sample of the liquid on which biochemical oxygen demand measurements are to be made can be injected through the fluid injection bore 80 into the sample holding chamber 18 for admixture with the culture medium.

Figure 3A:
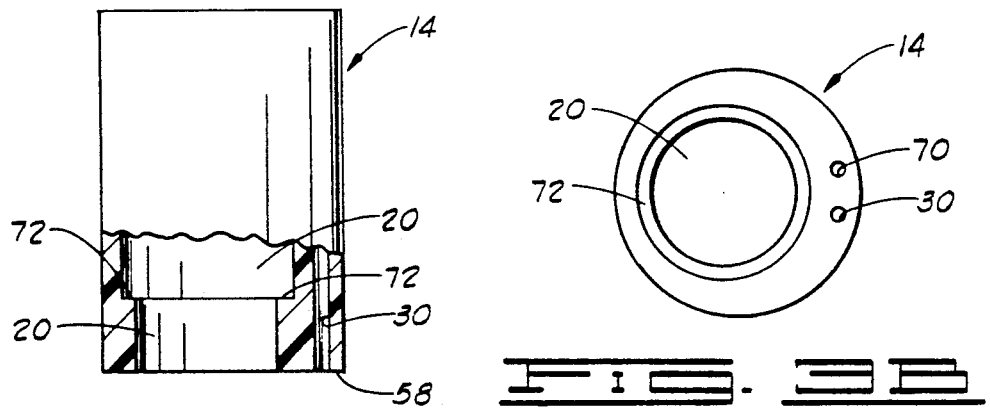
FIG. 3A is an enlarged, side elevational view, partially in cross section, of a plunger assembly for supporting a dissolved oxygen sensor or electrode in the cell body member.
Figure 3B:
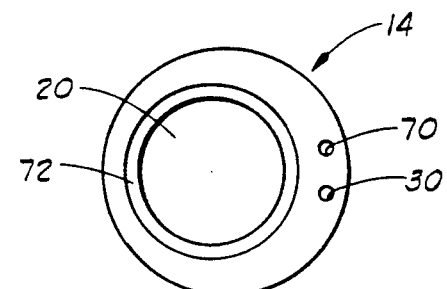
FIG. 3B is a top plan view of the plunger assembly of FIG. 3A.

Referring now to FIGS. 3A and 3B, the tubular plunger member 14 is provided with an electrode stop shoulder 72 disposed near the lower end 58 thereof. That is, the electrode stop shoulder 72 extends into the electrode receiving bore 20 of the tubular plunger member 14 and abuttingly engages and supports the dissolved oxygen sensor or electrode 22 substantially as shown in FIG. 1. Thus, the dissolved oxygen sensor or electrode 22 can be supported in a stable position within the electrode receiving bore 20 while insuring that contact is maintained between the dissolved oxygen sensor or electrode 22 and the homogeneous admixture of the culture medium and the sample liquid in the sample holding chamber 18.

The dissolved oxygen sensor or electrode 22 is supported in the electrode receiving bore 20 of the tubular plunger member 14 so that the distal end 24 thereof extends into the sample holding chamber 18 of the cell body member 12 and into contact with the culture medium and liquid sample disposed therein. Any suitable dissolved oxygen sensor or electrode capable of providing signals in response to the oxygen depletion of the culture medium and liquid sample can be employed as the dissolved oxygen sensor or electrode 22 of the cell assembly 10 of the present invention, such as the YSI 4004 Clark Oxygen Probe manufactured by Yellow Springs Instrument Co., Inc. of Yellow Springs, Ohio 45387.

Referring now to FIG. 4, the internal heat sink element 25, which is positionable in the annular space 60 formed about the sample holding chamber 18, and its relationship to the thermoelectric device 26 for maintaining the culture medium and liquid sample at a predetermined temperature, is shown in more detail. The internal heat sink element 25, which is desirably fabricated of aluminum, is provided with a rounded end portion 82 and an opposed end 83. The rounded end portion 82 of the internal heat sink element 25 is provided with a vertically disposed bore 84 extending therethrough. Thus, when the opposed second end 83 of the internal heat sink element 25 is aligned with the elongated slot 62 in the side wall 64 of the cell body member 12 and the rounded end portion 82 thereof is disposed within the annular space 60, the sample holding chamber 18 of the cell body member 12 is disposed within the bore 84.

The thermoelectric device 26, which is connected to the opposed end 83 of the internal heat sink element 25, is a Peltier cell device 86 having a first end portion 87 and an opposed second end portion 88 which comprises a plurality of spatially disposed fins 89. The first end portion 87 is formed of a first conductive material; and the second end portion 88, and thus the fins 89, are formed of a second conductive material. The first end portion 87 of the Peltier cell device 86 is connected to the opposed end 83 of the internal heat sink element 25 such that when the rounded end portion 82 of the internal heat sink element 25 is positioned in the annular space 60 of the cell body member 12 and the sample holding chamber 18 is disposed within the bore 84 thereof, the first and second end portions 87 and 88 of the Peltier cell device 86 extend through the elongated slot 62 formed in the side wall 64 of the cell body member 12. Thus, the internal heat sink element 25 and the Peltier cell device 86 cooperate to dissipate heat drawn from the homogeneous mixture of the culture medium and liquid sample during cooling of same; and the internal heat sink element 25 and the Peltier cell device 86 cooperate to draw heat from the atmosphere during heating of the homogeneous mixture of the culture medium and liquid sample.

The Peltier cell device 86 is operably connected to the microcomputer 66 (see FIG. 6) via electrical leads 90 and 91 so that when current flows between the first and opposed second end portions 87, 88 of the Peltier cell device 86 reversible heating or cooling occurs at the place of contact between the two dissimilar conductors constituting the first end and opposed second end portions 87 and 88 depending upon the direction of the flow of current therebetween.

Peltier cell devices are commercially available items well known in the art. Typically of a commercially available Peltier cell device which can be employed as the thermoelectric device 26 for selectively heating and cooling the culture medium and liquid sample in &.he sample holding chamber 18 in response to input from the microcomputer 66 is a Model MI 1013 T Peltier Cell manufactured by Marlow Industries of Dallas, Tex.

Figure 5:
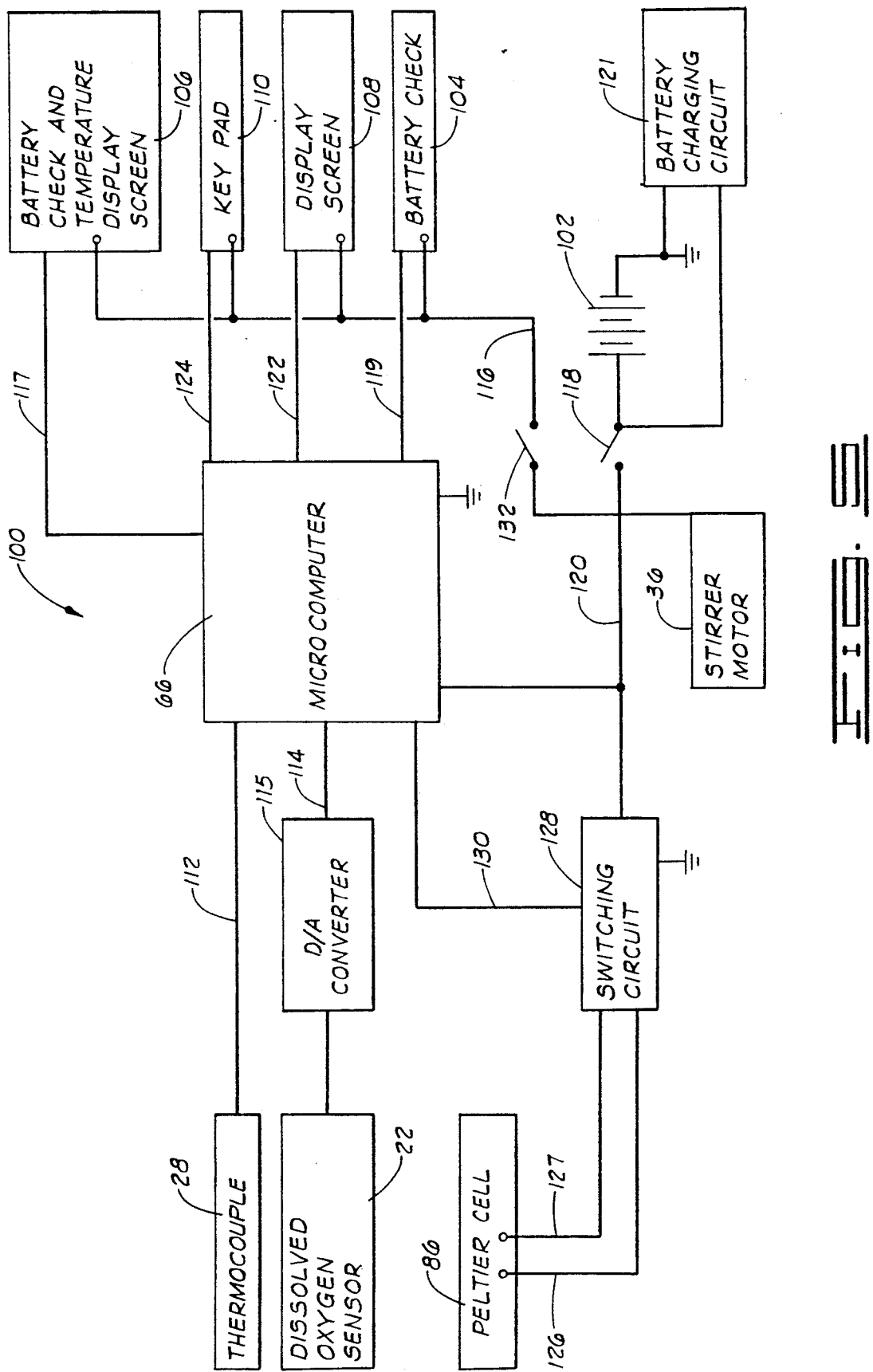
FIG. 5 is a block diagram of an apparatus for rapidly determining the biochemical oxygen demand of a liquid at an on-site location utilizing the cell assembly of FIG. 1.

Referring now to FIG. 5, a block diagram of a computer circuit 100 of the apparatus 11 for measuring the biochemical oxygen demand of a liquid sample is illustrated. The apparatus 11 includes the cell assembly 10, the thermocouple 28 and the dissolved oxygen sensor 22 mounted in the plunger chamber 16 of the tubular plunger member 14 to continuously provide electrical signals indicative of the temperature of the admixture of the culture medium and liquid sample in the sample holding chamber 18 of the cell body member 12 and the amount of oxygen dissolved in such admixture.

The computer circuit 100 comprises a programmed microcomputer 66 that is operated from a battery 102 (the battery is preferably rechargeable) and the battery 102 also provides a power supply for the Peltier cell device 86. The computer circuit 100 further comprises a battery checking device 104, a battery check and temperature display screen 106, a display screen 108 for providing instructions to the operator and for providing visual information as the BOD of the culture medium and the liquid sample and a keypad 110. (The microcomputer 66, a commercially available unit such as a Motorola Model 6805 or Motorola Model 68HC11 microcomputer, includes a ROM, not shown, wherein the program for the operation of the apparatus 11 is stored.) The thermocouple 28 is connected via line 112 to suitable I/O ports of the microcomputer 66 and the microcomputer 66 is programmed to periodically sample the temperature of the admixture of the culture medium and liquid sample in the sample holding chamber 18. The dissolved oxygen sensor 22 is connected through a conventional D/A converter 115 to suitable I/O ports of the microcomputer 66 via line 114. The microcomputer 66 is also programmed to periodically sample dissolved oxygen content of the admixture during the measurement of the biochemical oxygen demand (BOD) of a liquid sample as set forth hereinafter.

The battery check device 104 is conventional and receives power from the battery 102 on conducting path 116 when a power switch 118 for the computer circuit 100 is closed; and the battery check and display screen 106 is connected via the conducting path 116 to the battery 102 when the power switch 118 is closed. The battery checking device 104 is connected to the microcomputer 66 via suitable I/O ports and conducting path 119.

The battery and temperature display screen 106, a conventional LCD device that can present programmed messages from the microcomputer 66 to the operator indicative of the temperature of the culture medium and liquid sample, as well as the condition of the battery 102, is connected to the microcomputer 66 via suitable I/O ports and conducting path 117. For example, should the battery 102 be insufficiently charged the microcomputer 66 is programmed to output the message on the battery and temperature display screen 106 instructing the operator to "Replace Battery" so that the operator can open switch 118, replace the battery 102 and thereafter close the switch 118.

In the present invention, it is contemplated that the microcomputer 66, which receives power via the switch 118 on a conducting path 120, will be programmed to carry out a battery check each time the switch 118 is closed to initiate operation of the apparatus 11 to insure that the battery 102 will be in a state that will enable a BOD measurement to be completed without the need for changing the battery 102. That is, one will readily know if the battery 102 has a sufficient charge to, for example, provide the required current to the Peltier cell device 86 in order to maintain the admixture of the the culture medium and the liquid sample in the sample holding chamber 18 at the preselected temperature. To minimize the need for battery changes, the circuit 100 can include a conventional battery charging circuit 121 connected across the battery 102 to permit charging of battery 102 from household current between uses of the apparatus 11.

The display screen 108 is a conventional LCD device that can present programmed messages to the user of the apparatus 11 under the control of the microcomputer 66 to which the display screen 108 is connected via a suitable I/O port and conducting path 122. The messages present on the display screen 108 not only provide the operator with step by step procedures for carrying out the biochemical oxygen demand measurement using the apparatus 11, but also provides the operator with the BOD value of the liquid sample at the location or site of the test.

The key pad 110 is similarly conventional and is connected via a conducting path 124 to a suitable I/O port of the microcomputer 66 so that data and a selection of user messages programmed into the microcomputer 66 can be communicated thereto. In keeping with the object of providing a portable cell assembly for use in measuring the biochemical oxygen demand of a liquid at an on-site location that requires little user training, such messages are numbered. For example, calibration of the cell assembly 10 which involves introduction of a culture medium (i.e. a standard solution of glucose and glutamic acid which has a known BOD of 200 ppm) into the sample holding chamber 18, can be assigned the number "1" while the analysis of a sample of a liquid to be tested can be assigned the number "2". Thus, at a branch point in the program where the operator must decide whether a calibration step or an analysis step is to be carried out, the microcomputer 66 outputs the message "1—Calibration or 2—Analysis" to the display screen 108 and the operator need press only one key, labeled with the number "1" or "2" to provide the appropriate message to the microcomputer 66. Since the messages are numbered, the keypad 110 can comprise keys corresponding only to the numerals 1 through 9, the decimal point and an "enter" key to provide a saving in the cost of manufacture of the apparatus 11.

Control of the Peltier cell device 86, which receives power from the battery 102 via the conducting path 120 and conducting paths 126 and 127, is effected by a conventional switching circuit 128, connecting the path 120 and the system ground to the path 126, that is controlled by the microcomputer 66 via a suitable I/O port and a conducting path 130. In particular, the switching circuit 128 responds to signals from the microcomputer 66 to select the direction in which a current is passed through the Peltier cell device 86 and to complete a circuit between the Peltier cell device 86 and the battery 102 to selectively heat or cool the culture medium and liquid sample in the sample holding chamber 18 of the cell body member 12.

In addition to the above components, the circuit 100 is comprised of the magnetic stir motor 36 used to rotate the micro stir bar 34 in the sample holding chamber 18 as discussed above. The magnetic stir motor 36 is connected to the battery 102 via a switch 132 mounted on a control panel 140 of a housing 142 (see FIG. 6A) and marked so that the user of the apparatus 11 can stir the liquid sample and the culture medium in the sample holding chamber 18 of the cell assembly 10 by merely closing the switch 132.

Referring now to FIGS. 6A and 6B, the apparatus 11 further comprises the housing 142 having a body member 144, the control panel 140 supported by the body member 144 and a closure member 146. The closure member 146 is pivotally connected to an upper side portion 148 of the body member 144 via hinges 150, 152 such that the closure member 146 is movable between a first position (wherein the closure member 146 is disposed in a noncovering relation relative to the body member 144 as shown in FIG. 6A) and a second position (wherein the closure member 146 is disposed in a covering position relative to the body member 144 substantially as shown in FIG. 6B). The closure member 146 can be secured in the second covering position by a plurality of latch members 154, 156 in a customary manner. A handle 158 is secured to the closure member 146 for permitting the user to readily transport the cell assembly 10 from one location to another.

Referring more specifically to FIG. 6A, the body member 144 of the housing 142 is provided with an interiorly disposed cavity 160 and the control panel 140 is supported by, the body member 144 so as to be substantially flush with an upper portion of the the body member 144 substantially as shown. The cell body member 12, the magnetic stir motor 36 and the microcomputer 66 are secured within the interiorly disposed cavity 160.

The control panel 140 is provided with the battery check and display screen 106, the display screen 108, the key pad 110, switches 118 and 132 and a plurality of female connectors 162, 164, 166 and 168, each of which is electrically connected to the microcomputer 66. An orifice 170 is formed in the control panel 140 so as to be aligned with the cell body member 12 and the magnetic stir motor 36. The female connectors 162, 164 matingly receive male connectors 172, 174 (see FIG. 1) of the dissolved oxygen sensor 22 so that electrical connection is established between the dissolved oxygen sensor 22 and the microcomputer 66 when the dissolved oxygen sensor 22 is positioned in the electrode receiving bore 20 of the tubular plunger member 14 and the microcomputer 66 is activated by the turning on of the power switch 118. The female connectors 166 and 168 can be employed to matingly receive male connectors (not shown) of a chart recorder (also not shown) which can be electrically connected to the microcomputer 66 so that the data generated can be recorded.

The cell body member 12 can be secured to the control panel 140, and thus within the interiorly disposed cavity 160 of the body member 144 by providing a plurality of apertures (not shown) in the control panel 140 which are disposed about the orifice 170 so as to be alignable with the openings 52 and 54 in the flange 50 of the cell body member 12. Bolts 176, 178 can then be positioned through aligned apertures (not shown) in the control panel 140 and the openings 52, 54 in the flange 50 of the cell body member 12 and secured in place by threadably engaging a lock nut (not shown) on each of the bolts.

Any suitable means can be employed for securing the magnetic stir motor 36 within the interiorly disposed cavity 160 of the body member 144. For example, the magnetic stir motor 36 can be secured therein via a plurality of self-tapping screws, a suitable adhesive, or can be supported in place via the recess 68 formed in the lower end portion 40 of the cell body member 12.

Procedure For Determining The Biochemical Oxidation Demand Of A Liquid Using The Apparatus Of The Present Invention The apparatus 11, which is a self-contained apparatus, is transported to the site where the liquid to be tested is located. Once on site, the operator unlatches the closure member 146 and move same to the first position so that the control panel 140 is accessible to the operator.

To commence the testing procedure the operator turns the apparatus 11 on with the switch 118. The microcomputer 66 then checks the condition of the battery 102. If the battery 102 is low an appropriate message is transmitted from the microcomputer 66 to the battery check and temperature display screen 106 so that the operator is advised of the necessity of charging the battery 102 prior to continuing, or replacing the battery 102. If the battery 102 is sufficiently charged the microcomputer 66 will provide a message to the display screen 108 wherein the operator is instructed to "Place Culture In Sample Chamber". Thereafter, the operator injects the culture medium into the sample holding cavity 18 and strikes the key designated as the "Enter" key on the keypad 110.

After the culture medium has been placed into the sample chamber 18 of the cell assembly 10, the magnetic stir motor 36 and the Peltier cell device 86 are activated. It should be noted that the stirring speed of the culture medium, as well as the admixture of the culture medium and the liquid sample is not critical as long as the stirring rate is constant during the measurements made using the apparatus 11. Further, the temperature employed in carrying out the measurements is not critical but must be constant in order to obtain valid data. However, it is generally desirable to carry out the measurements at a temperature of about 20° C.

The microcomputer 66 next provides a signal to the display screen 108 which reads "1—Calibration or 2—Analysis". Depending on whether the apparatus 11 is being calibrated or an analysis is being made on a liquid sample, the operator will enter either the number "1" or "2" into the microcomputer 66 via the key pad 110. If the operator enters the instruction "1—Calibrate" the following calibration procedure is followed.

Calibration

A factor k, which will be described in more detail hereinafter, must be arrived at experimentally through a calibration run. The value of k must be retained in the memory of the microcomputer 66 in order to determine the actual biochemical oxidation demand ($BOD_a$) of the liquid sample being measured.

In calibrating the apparatus 11, the temperature is allowed to equilibrate. When the microcomputer 66 determines that the temperature has equilibrated through measurements obtained from the thermocouple 28, the microcomputer 66 provides a message to the display screen 108 which instructs the operator to "insert electrode plunger". The tubular plunger member 14, having the dissolved oxygen sensor or electrode 22 supported within the electrode receiving bore 20 thereof, is then positioned within the plunger chamber 16 of the cell body member 12, and the dissolved oxygen sensor 22 is connected to the microcomputer 66 by connecting the male connectors 172, 174 of the dissolved oxygen sensor 22 to the female connectors 162 and 164.

The dissolved oxygen (DO in mv) consumption is measured by the dissolved oxygen electrode sensor 22 and monitored by the microcomputer 66. When a stable rate of dissolved oxygen consumption at the time ($T_1$) is achieved the rate ($R_1$), the dissolved oxygen (DO) and the time ($T_1$) are stored in the memory of the microcomputer 66 and the microcomputer 66 provides a signal to the display screen 108 which instructs the operator to "Inject 30 Microliters Of Calibration Solution".

Once the operator has injected the 30 microliters of calibration solution into the sample holding chamber 18 via the fluid injection bore 70, the dissolved oxygen consumption rate will initially increase and, as time passes, return to rate $R_1$ at time $T_2$. Once the oxygen consumption rate has returned to $R_1$ the conversion constant k can then be calculated by the microprocessor 66 in accordance with the formula:

$$k = 15/[DO_1 - DO_2 - R_1(T_2 - T_1)]$$

When the value of the conversion constant k has been determined by the microcomputer 66 it is stored in the memory of the microcomputer 66 for sequential use in the analysis of the liquid sample.

Once the calibration of the apparatus 11 has been completed, the tubular plunger member 14 is removed from the cell body member 12 and the cell body member 12, the tubular plunger member 14, and the dissolved oxygen sensor 22 are thoroughly rinsed with distilled water to provide a clean test cell for sequence analysis of the liquid sample.

Analysis of Liquid Sample After Calibration Of The Apparatus

The microcomputer 66, which has remained in an operational mode, then provides a signal to the display screen 108 and instructs the operator to "Place Culture in Sample Chamber". The operator then injects the culture medium into the sample chamber 18 and strikes the "Enter" key of the key pad 110. The magnetic stir motor 36 and the Peltier cell device 86 are then activated so that the culture medium in the sample holding chamber 18 is agitated by the micro stir bar 34.

The microcomputer 66 then provides a message to the operator via the display screen 108 which again reads "1—Calibration or "2—Analysis". Since the apparatus 11 has been previously calibrated and the conversion constant k stored in the memory of the microcomputer 66, the operator strikes the key designated as "2" on the key pad 110 to provide input data to the microcomputer 66 that an analysis is to be made.

The microcomputer 66 monitors the temperature of the culture medium in the sample holding chamber 18. Once the temperature has become equilibrated, the microcomputer 66 provides a signal to the display screen 108 which instructs the operator to "Insert Electrode Plunger".

Upon receiving the instruction, the operator inserts the tubular plunger member 14 into the plunger chamber 16 of the cell body member 12, the dissolved oxygen sensor or electrode 22 having previously been positioned within the electrode receiving bore 20 of the tubular plunger member 14. Thereafter, the dissolved oxygen sensor 22 is operably connected to the microcomputer 66 by connecting the male connectors 172 and 174 of the dissolved oxygen sensor 22 to the female connectors 162 and 164.

The microcomputer 66 monitors the dissolved oxygen (DO in mv) and consumption rate (DO/T) of the dissolved oxygen in the culture medium. Once a stable rate at time $T_1$ is achieved rate ($R_1$), DO and time ($T_1$) are stored in the memory of the microcomputer 66 and a message is provided to the operator via the display screen 108 which reads "Injects Sample". Upon receiving such message, the operator injects a sample of the liquid on which the biochemical oxygen demand measurements (BOD) are to be made into the sample holding chamber 18 via the fluid injection bore 70. That is, a hypodermic needle is positioned within the fluid injection bore 70 so that the operator can inject the required amount of liquid sample into the sample holding cavity 18.

Once the operator has injected the liquid sample into the sample holding cavity 18 a homogeneous admixture of the culture medium and liquid sample is achieved by the agitation resulting from rotation of the micro stir bar 34 in the sample holding chamber 18. The dissolved oxygen sensor 22 continues to provide signals to the microcomputer 66 which indicate that the oxygen consumption rate of the homogeneous mixture has increased. Monitoring of the oxygen consumption rate is continued until same returns to the rate $R_1$ at a time $T_2$. Once the consumption rate has returned to $R_1$ the unadjusted biochemical oxygen demand ($BOD_u$) can be calculated by the microcomputer 66 as follows:

$$BOD_u = K[DO_1 - DO_2 - R_1(T_2 - T_1)]$$

If the dissolved oxygen present in the sample drops below 1 mv the microcomputer 66 provides a message to the operator via the display screen 108 which instructs the operator to "Dilute Sample And Run Again". On the other hand, if $DO_2 - DO_1$ is less than 5 mv the microcomputer 66 will also provide a message to the operator via the display screen 108 which reads "Use A Larger Sample And Run Again".

When the microcomputer 66 determines that the DO is between 1 and 5 mv the microcomputer 66 will provide a message to the operator via the display screen 108 to "Enter Sample Size In ul". The operator then enters the sample size (S) into the microcomputer 66 by striking the appropriate key of the key pad 110.

Once the sample size (S) has been entered, the microcomputer 66 instructs the operator via the display screen 108 to "Enter Dilution Factor 1/X". The operator, in accordance with the instructions from the microcomputer 66, enters the dilution factor into the microcomputer 66 by striking the appropriate keys of the key pad 110. Upon entry of the dilution factor, the microcomputer 66 calculates actual BOD ($BOD_a$) as follows:

$$BOD_a = BOD_u (X) (2000/S)$$

and displays the actual BOD on the display screen 108.

In carrying out biochemical oxygen demand measurements on a liquid sample using the apparatus 11 of the present invention the oxygen electrode selected requires that a voltage of 0.8 v be maintained across the leads during the calibration and measuring procedures. Further, a physical record of the data processed by the microcomputer 66 can be obtained by connection of a strip chart recorder (not shown) to the female connectors 166 and 168 supported by the control panel 140 and which are electrically connected to the microcomputer 102 of the apparatus 11.

The unique design of the apparatus 11, together with the design of the cell assembly 10, permits one to easily and rapidly make biochemical oxidation demand measurements on a liquid at an on-site location. Further, it will be clear that the present invention is well adapted to carry out the objects and attain the ends and advantages mentioned as well as those inherent therein. While a presently preferred embodiment has been described for purposes of this disclosure, numerous changes may be made which will readily suggest themselves to those skilled in the art and which are encompassed in the spirit of the invention disclosed and as defined in the appended claims.

What is claimed is:

1. A cell assembly for use in determining the biological oxidation demand of a liquid sample in the presence of a culture medium, the cell assembly comprising:

a cell body member having a vertically disposed plunger chamber and a sample holding chamber communicating with the plunger chamber, the cell body member further including a peripherally extensive plunger stop shoulder formed between the plunger chamber and the sample holding chamber;

electrode means for generating a signal in proportion to the amount of dissolved oxygen content of the liquid sample and the culture medium in the sample holding chamber;

plunger means extensive into the plunger chamber for supporting the electrode means such that the electrode means extends into the sample chamber and into contact with the liquid sample and the culture medium disposed therein, the plunger means comprising:

a tubular plunger member having an upper end, a lower end, an electrode receiving bore longitudinally extensive therethrough, a thermocouple receiving bore, and a spatially disposed fluid injection bore extending longitudinally therethrough, each of the thermocouple receiving bore and the fluid injection bore openly communicating with the sample holding chamber of the cell body member; and a peripherally extensive electrode stop shoulder disposed near the lower end of the tubular plunger member so as to extend into the electrode receiving bore and abuttingly engage the electrode means, the plunger stop shoulder and the electrode stop shoulder cooperating to provide the sample holding chamber with a predetermined volume when the electrode means is disposed within the electrode receiving bore of the tubular plunger member and the tubular plunger member is disposed within the plunger chamber of the cell body member;

stirrer means for agitating the liquid sample and culture medium in the sample holding chamber at a substantially constant rate to provide a substantially homogeneous mixture of the liquid sample and the culture medium;

temperature of the liquid sample and the culture medium in the sample holding chamber, the temperature sensor means comprising:

a thermocouple disposed within the thermocouple receiving bore of the tubular plunger member for generating a signal indicative of the temperature of the homogeneous mixture of the liquid sample and the culture medium in the sample holding chamber; and temperature control means supported by the cell body member in close proximity to the sample holding chamber for selectively heating and cooling the liquid sample and culture medium in the sample holding chamber in order to maintain same at a predetermined temperature.

2. The cell assembly of claim 1 wherein the temperature control means for selectively heating and cooling the homogeneous mixture of the liquid sample and the culture medium in the sample holding chamber comprises a Peltier cell device mounted on the cell body member.

3. The cell assembly of claim 2 wherein the cell body member is provided with an annular space extensive from a lower end thereof so as to be disposed about the sample holding chamber, the annular space defining an internal heat sink for the homogeneous mixture in the sample holding chamber, the cell body member being further provided with an elongated slot extensive through one side wall and openly communicating with the annular space, and wherein the cell assembly further comprises an internal heat sink element positionable within the annular space, the internal heat sink element connected to the Peltier cell device and cooperating with the Peltier cell device for dissipating heat drawn from the homogeneous mixture of the culture medium and the liquid sample during cooling of same and for drawing heat from the atmosphere during heating of the homogeneous mixture of the culture medium and the liquid sample.

4. The cell assembly of claim 3 wherein the internal heat sink element is characterized as having a rounded end portion and an opposed end portion, the rounded end portion having a vertically disposed bore extending therethrough, and wherein the Peltier cell device is fabricated of a first conductive material and a second conductive material, the portion of the Peltier cell device fabricated of the first conductive material connected to the opposed end portion of the internal heat sink element, the portion of the Peltier cell device fabricated of the second conductive material defining a plurality of fins.

5. An apparatus for rapidly determining the biochemical oxidation demand of a liquid at an on-site location, the apparatus comprising:

a cell body member having an upper end, an opposed lower end and a vertically disposed plunger chamber formed therein such that an opposed lower end of the plunger chamber terminates a distance from the opposed lower end of the cell body member;

a tubular plunger member having an electrode receiving bore extensive therethrough, the tubular plunger member insertable a selected distance into the plunger chamber to form a test chamber in a lower portion of the plunger chamber for receiving a culture medium and a liquid sample;

electrode means supported in the electrode receiving bore of the tubular plunger member for generating a signal in proportion to the amount of dissolved oxygen content of the culture medium and the liquid sample in the test chamber;

temperature means supported by the cell body member for measuring and controlling the temperature of the culture medium and the liquid sample in the test chamber at a temperature; and a computer connected to the electrode means and to the temperature means for monitoring the temperature of the culture medium and liquid sample in the test chamber, for controlling the temperature of the culture medium and liquid sample in the test chamber at the predetermined temperature, for determining the dissolved oxygen content of the culture medium and the liquid sample in the test chamber and calculating the biochemical oxygen demand of the liquid sample.

6. The apparatus of claim 5 wherein the temperature control means comprises:

a thermocouple communicating with the culture medium and the liquid sample in the test chamber; and a Peltier cell device disposed substantially adjacent the test chamber, the thermocouple and the Peltier cell device electrically connected to the computer which is programmed to monitor the temperature of the culture medium and the liquid sample via input signals from the thermocouple and provide control signals to the Peltier cell device to maintain the temperature of the culture medium and the liquid sample at a substantially constant value.

7. The apparatus of claim 6 further comprising an internal heat sink element disposed about the test chamber, the internal heat sink element connected to the Peltier cell device for dissipating heat drawn from the culture medium and liquid sample during cooling of same and for drawing heat from the atmosphere during heating of the culture medium and liquid sample.

8. The apparatus of claim 6 wherein the electrode means comprises:
 a dissolved oxygen sensor mounted within the electrode receiving bore of the tubular plunger member so as to contact the culture medium and the liquid sample in the test chamber and provide signals indicative of the dissolved oxygen content of the culture medium and the liquid sample, the dissolved oxygen sensor connected to the computer which is programmed to determined the dissolved oxygen content of the culture medium and the liquid sample from the signals provided thereto by the dissolved oxygen sensor.

9. The apparatus of claim 8 wherein the cell body member is provided with a peripherally extensive plunger stop shoulder protruding into a lower portion of the plunger chamber for supportingly engaging the lower end of the tubular plunger member.

10. The apparatus of claim 9 wherein the tubular plunger member further comprises a peripherally extensive electrode stop shoulder disposed near the lower end thereof so as to extend into the electrode receiving bore and supportingly engage the dissolved oxygen sensor, the plunger stop shoulder of the cell body member and the electrode stop shoulder of the tubular plunger member cooperating to provide the test chamber with a predetermined volume when the dissolved oxygen sensor is disposed within the electrode receiving bore of the tubular plunger member and the tubular plunger member is disposed in the plunger chamber of the cell body member.

11. The apparatus of claim 10 further comprising:
 a stirrer assembly electrically connected to a power source so as to be actuated by the power source and thereby agitates the liquid sample and culture medium in the test chamber at a substantially constant rate to provide a substantially homogeneous mixture of the liquid sample and the culture medium.

12. The apparatus of claim 11 wherein the tubular plunger member is further provided with a thermocouple receiving bore extending longitudinally therethrough and a spatially disposed fluid injection bore extending longitudinally therethrough, each of the thermocouple receiving bore and the fluid injection bore openly communicating with the test chamber of the cell body member.

13. The apparatus of claim 12 wherein the cell body member is provided with an annular space disposed about the test chamber of the cell body member, and an elongated slot extensive through one side wa and openly communicating with the annular space, and wherein the apparatus further comprises:
 an internal heat sink element having a rounded end portion and an opposed end portion, the rounded end portion having a vertically disposed bore extending therethrough, the rounded end portion positionable within the annular space disposed about the test chamber such that the test chamber is disposed within the bore thereof, the second end portion of the internal heat sink connected to the Peltier cell device such that the Peltier cell device is disposed through the elongated slot in the side wall of the cell body member.

14. The apparatus of claim 13 further comprising: power means for actuating the computer.

15. The apparatus of claim 14 further comprising:
 a housing having a body member defining an interiorly disposed cavity, a control panel supported in the upper portion of the body member, the interiorly disposed cavity adapted to receive the computer and the cell body member, the control panel having a plurality of display screens operably connected to the computer, a keypad operably connected to the computer for providing input data to the computer, and a plurality of pin connectors for connecting the electrode means to the computer, the control panel having an orifice therein adapted to receive the tubular plunger member of the cell body member such that the tubular plunger member can be inserted into the plunger cavity of the cell body member; and
 means for connecting the cell body member to the control panel such that the cell body member is maintained in a secure stable position in the interiorly disposed cavity of the housing.

16. The apparatus of claim 15 wherein the stirrer means comprises:
 a magnetic stirrer bar positionable in the sample holding cavity; and
 a stirrer motor supported in the interiorly disposed cavity of the housing so as to be aligned with the orifice in the control panel and to supportingly engage the lower end of the cell body member.

17. The apparatus of claim 16 wherein the cell body member is further provided with a peripherally extensive flange disposed about the upper end of the cell body member for cooperating with the means for connecting the cell body member to the control panel so that the orifice in the control panel is aligned with the plunger receiving cavity in the cell body member.

18. The apparatus of claim 17 wherein the lower end of the cell body member is provided with a centrally disposed recess communicating with the annular space disposed about the test chamber such that upon connecting the peripherally extensive flange of the cell body member to the control panel the stirrer motor is positionable within the centrally disposed recess for supportingly engaging the cell body member and thereby cooperating with the peripherally extensive flange of the cell body member and the means for connecting the flange of the cell body member to the control panel to stabilize the cell body member in the interiorly disposed cavity of the housing.

19. The apparatus of claim 18 wherein the housing further comprises:
 a closure member pivotally connected to an upper side portion of the housing such that the closure member is movable between a first position and a second position, in the first position the closure member permitting substantially unrestricted access to the control panel, in the second position the closure member being disposed in a covering position of the control panel; and
 latch means for securing the closure member to the housing in the second position.

20. The apparatus of claim 19 wherein the housing further comprises:
 handle means for permitting one to readily transport the apparatus.

* * * * *

UNITED STATES PATENT AND TRADEMARK OFFICE
CERTIFICATE OF CORRECTION

PATENT NO. : 5,085,759
DATED : February 4, 1992
INVENTOR(S) : Alan R. Harker

It is certified that error appears in the above-indentified patent and that said Letters Patent is hereby corrected as shown below:

Column 6, line 48, delete "&.he" and substitute therefor --the--;

Column 13, lines 43-45, delete

"temperature of the liquid sample and the culture medium in the sample holding chamber, the temperature sensor means comprising:"

and substitute therefor:

--temperature sensor means for providing an indication of the temperature of the liquid sample and the culture medium in the sample holding chamber, the temperature sensor means comprising:--; and Column 15, line 58, delete "wa" and substitute therefor --wall--.

Signed and Sealed this

Seventeenth Day of May, 1994

Attest:

BRUCE LEHMAN

*Attesting Officer*     *Commissioner of Patents and Trademarks*